United States Patent
Chorush et al.

[11] Patent Number: 6,032,513
[45] Date of Patent: Mar. 7, 2000

[54] APPARATUS AND METHOD FOR MEASURING CONTAMINANTS IN SEMICONDUCTOR PROCESSING CHEMICALS

[75] Inventors: Russell A. Chorush, Plano; Jeremiah D. Hogan, Richardson; Deepta Varadarajan, Allen, all of Tex.

[73] Assignee: Texas Instruments Incorporated, Dallas, Tex.

[21] Appl. No.: 09/107,109

[22] Filed: Jun. 30, 1998

Related U.S. Application Data

[60] Provisional application No. 60/051,275, Jun. 30, 1997.

[51] Int. Cl.[7] .......................... G01N 30/74; G01N 27/62; H01J 49/42; G01D 55/44
[52] U.S. Cl. .......................... 73/23.35; 73/23.37; 356/316; 324/468; 436/153; 422/89; 250/326
[58] Field of Search .............................. 73/23.35, 23.37, 73/23.4, 61.58; 356/313, 316; 436/153, 161; 210/656; 422/70, 89; 250/326; 324/455, 468

[56] References Cited

U.S. PATENT DOCUMENTS

| | | | |
|---|---|---|---|
| 4,586,368 | 5/1986 | Rice et al. .............................. | 73/23.1 |
| 4,737,465 | 4/1988 | Bond et al. ................................ | 436/73 |
| 5,012,052 | 4/1991 | Hayes ....................................... | 250/288 |
| 5,014,009 | 5/1991 | Arimoto et al. .......................... | 324/468 |
| 5,031,449 | 7/1991 | Kuwana et al. ...................... | 73/61.1 R |
| 5,142,144 | 8/1992 | Remo et al. ............................. | 250/288 |
| 5,152,176 | 10/1992 | Bryselbout et al. ................... | 73/23.41 |
| 5,198,988 | 3/1993 | Dorr et al. ............................... | 364/497 |
| 5,394,092 | 2/1995 | Wentworth et al. .................... | 324/464 |
| 5,684,300 | 11/1997 | Taylor et al. ............................ | 250/286 |
| 5,728,586 | 3/1998 | Platzer .................................... | 436/153 |
| 5,886,346 | 3/1999 | Makarov .................................. | 250/291 |

*Primary Examiner*—Hezron Williams
*Assistant Examiner*—J. David Wiggins
*Attorney, Agent, or Firm*—Wade James Brady III; Richard L. Donaldson

[57] ABSTRACT

An trace analyzer apparatus and method useful in semiconductor processing for measuring trace impurities in gases and liquids comprising a gas chromatograph serving to replace a bulk gas in a composition of bulk gas including contaminants in a bulk gas stream with a carrier gas having a higher ionization potential than that of said contaminants, where such gas chromatograph is connected to a hollow electrode (14) for initiating ionization of said contaminants by electrical discharge, where such electrode is electrically isolated from a source housing (44) and adjacent to a skimmer plate (16) that ionizes trace contaminants that are measured using a mass spectrometer, is disclosed.

23 Claims, 2 Drawing Sheets

APPARATUS AND METHOD FOR MEASURING CONTAMINANTS IN SEMICONDUCTOR PROCESSING CHEMICALS

This application claims priority under 35 U.S.C. § 119 (e)(1) of provisional patent application number 60/051,275 filed Jun. 30, 1997.

TECHNICAL FIELD OF THE INVENTION

The present invention relates in general to the field of quantitating trace impurities in gases and liquids and, in particular, to an apparatus for performing atmospheric ionization on a gas stream exiting a chromatographic column.

BACKGROUND OF THE INVENTION

Without limiting the scope of the invention, the background is described in connection with the analysis of gases used in the manufacture of integrated circuits.

Heretofore, in this field, a variety of analytical methods are used in the trace analysis of gases used in the manufacture of integrated circuits. Principal figures of merit for these techniques include the extent to which they can analyze the wide variety of gases used in semiconductor manufacture, their breadth of sensitivity to the variety of contaminants thought detrimental to semiconductor processing, and their ability to quantitative trace levels of those contaminants. Among the most sensitive methods for quantitation of trace impurities is the atmospheric-pressure ionization mass spectrometer, often providing several orders of magnitude reduced limits of quantitation over alternative analytical methodologies.

The atmospheric-pressure ionization mass spectrometer relies upon the selective ionization of contaminants at atmospheric pressure with subsequent mass separation and detection using the mass spectrometer. The ionization process consists of the removal of a negatively-charged electron from a neutral molecule to create a positively-charged ion. Although the primary ionization step occurs without selectivity, the unusually high (atmospheric) pressure ensures a multitude of collisions between charged and uncharged particles resulting in the opportunity for secondary, and potentially much more selective, ionizations. The unselective primary ionizations are almost exclusively of the pure bulk gas. Consequently, a requirement for the selective secondary ionization of the uncharged trace contaminants is the energetic favorability of a charge (electron) transfer between an ionized bulk gas molecule and an uncharged contaminant molecule.

The ionization potential (IP) describes the energy required to remove the most weakly held electron from an uncharged molecule and, conversely, the energy released when an electron is supplied to a positively-charged ion. Therefore, a requirement for energetic feasibility of this process is that the IP of the contaminant of interest must be lower than that of the bulk gas. Under this condition, the ionization process can proceed with tremendous selectivity, often allowing unit ionization efficiencies for the relatively low-IP contaminant. Additionally, providing that the various contaminant IPs are appropriate, the broad detection capabilities of the mass spectrometer lend the technique to concurrent detection of a wide variety of contaminants.

Unfortunately, the IP requirement has significantly limited the scope of use for conventional atmospheric-pressure ionization mass spectrometers. While analysis of highly-detrimental contaminants such as oxygen (IP=12.07 eV) and moisture (IP=12.61 eV) in nitrogen (IP=15.6 eV), argon (IP=15.8 eV) and He (IP=24.6 eV, highest known) are typical, analysis of contaminants such as nitrogen and moisture in oxygen is unavailable. Similarly, this limitation has excluded the use of this technique to analyze contaminants of interest in the broad variety of typically low IP semiconductor process gases, such as ammonia (IP=10.2 eV), arsine (IP=10.3 eV) and borane (IP=11.4 eV).

A desirable improvement would be a modification which retains the exceptional breadth of sensitivity to various contaminants and limits of quantitation while allowing for analysis of a greater variety of bulk gases. This, in turn, would provide a reduced cost of ownership in the form of a reduced need for competing technologies to provide these additional analytical capabilities. However, it is the same energetic of the relative IPs which lends atmospheric-pressure ionization its inherent limits of quantitation that precludes its use in this extension to low ionization bulk gases.

Therefore, what is needed is a method for atmospheric-pressure ionization which does not rely on a desirable relationship between the ionization potential of the trace impurity and the ionization potential of the bulk gas.

SUMMARY OF THE INVENTION

The present invention solves the problems associated with limitations based on relative ionization potentials, wherein gaseous contaminants can be analyzed in gases using atmospheric-pressure ionization mass spectrometry. An atmospheric-pressure ionization source design is disclosed which allows coupling of a mass spectrometer to a gas chromatographic column used to separate contaminants from the bulk gas in a high ionization potential carrier gas.

In one embodiment the apparatus for measuring contaminants of the present invention comprises a gas chromatograph that is connected to a hollow electrode and which is adjacent to and electrically isolated from a plate, such as a skimmer plate. The ionized gases produced by a corona discharge created by the difference in electrical potential between the hollow electrode and the plate is drawn into a mass spectrometer that isolates particular ions which are measured as an ionic current by a detector.

The hollow electrode is a low work function metal. Examples of low work function metals for use with the present invention include platinum, stainless steel, tungsten, or silver.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

Figure 1:
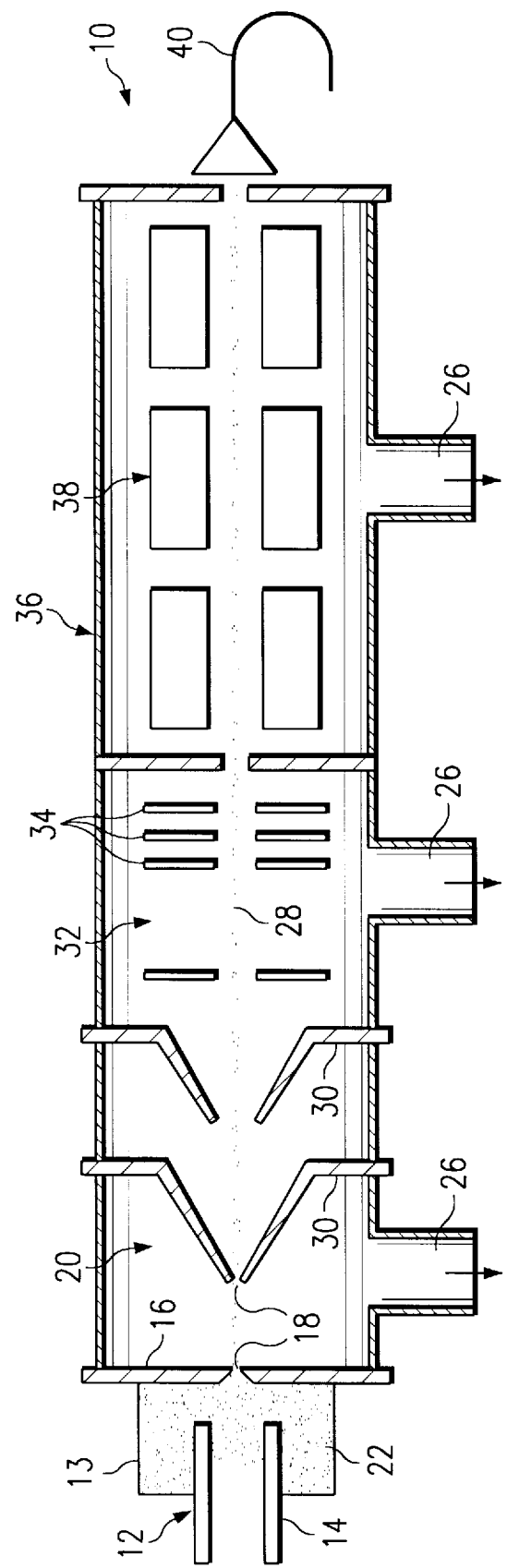
FIG. 1 is a cross sectional view of a atmospheric pressure ionization source coupled to an mass spectrometer of the present invention.

FIG. 1 depicts a cross section of the atmospheric pressure ionization mass spectrometer 10 of the present invention. An atmospheric pressure ionization mass spectrometer 10 has an ion source that has a hollow needle electrode 14 that is charged to a voltage of about 3 to 100 kilovolts (either positive or negative) depending on the type of gas to be analyzed. A skimmer plate 16 is disposed adjacent to a hollow needle electrode 14, and serves as a reference electrode. The skimmer plate 16 has an aperture 18 that permits ionized gas to flow into a first low pressure region 20.

The electric potential between hollow needle electrode 14 and skimmer plate 16 create a corona discharge that ionizes balance gas 22 entering the ion source chamber 13. The hollow needle 14 serves as both the electrode and the gas inlet. The balance gas 22 is generally a gas of high ionization potential, for example, helium, nitrogen or argon. Contaminants of interest exist in the balance gas 22. As a result of the ionization of the balance gas 22, a charge exchange takes place between the balance gas 22 and the lower ionization potential contaminants in the balance gas 22. Gas outlet 26 removes the majority of balance gas 22 from the first low pressure region 20, however, a portion of balance gas 22 is ionized as it passes through the corona discharge created by hollow needle 14 and the skimmer plate 16.

An ion beam 28 is produced as the ionized contaminants and ionized balance gas 22 pass through the aperture 18 into the first low pressure region 20. The first low pressure region 20 is at approximately 1–2 torr, a pressure which is achieved by rough pumping the first low pressure region 20. The ionized contaminants and the ionized balance gas 22 are drawn through the skimmer plate 16 by the viscous flow of the balance gas 22 into the first low pressure region 20.

A small proportion of the ion beam 28 is drawn past a skimmer cone 30 into a second low pressure region 32 which is evacuated by a high vacuum pump (not depicted) to achieve a pressure of about $10^{-4}$ torr. One or more skimmer cones 30 may be found in the second low pressure region 32, depending on the specific application of use as will be known to those of skill in the art of mass spectrometry. Ion focusing lenses 34 are located within the second low pressure region 32 and serve to focus the ion beam 28 into the third low pressure region 36. The electrostatic potentials created by the ion focusing lenses 34 focuses and directs the ion beam 28 into the mass filter 38. The pressure within the third low pressure region 36 is of about $10^{-6}$ torr and is produced using a second high vacuum pump (not depicted). The mass filter 38 may be a quadrapole mass filter or a magnetic or electronic sector filter, for example. In operation, the mass filter 38 selectively allows specific ions within the ion beam 28 to reach the detector 40 based on the mass-to-charge ratio of the ion.

Figure 2:
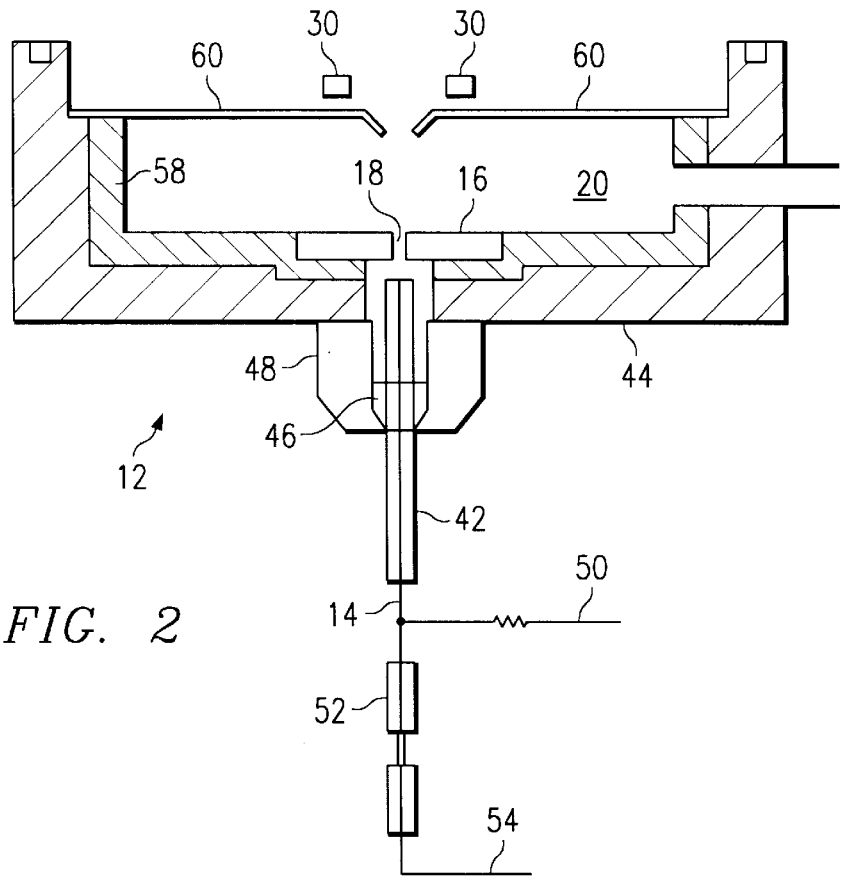
FIG. 2 is a cross sectional close-up view of the hollow needle electrode of the present invention.

FIG. 2 depicts a cross section of the ion source 12 of the present invention. Hollow needle electrode 14 is encased in an insulator 42 that electrically isolates the hollow needle electrode 14 from the source housing 44. In one embodiment the hollow needle 14 is made of an electrically conductive material that has a low work function, such as platinum, stainless steel, tungsten or silver. The insulator 42 can be a ceramic, glass, or any material with a sufficiently high dielectric constant to provide electrical isolation between the hollow needle electrode 14 and the source housing 44. The hollow needle electrode 14 is cemented in place within the insulator 44 by any material that provides vacuum isolation and that does not out gas.

The insulator 42 is held in place by a deformable ferrule 46 that is impermeable to gas, such as, vespel®, polypropylene, teflon® coated, or graphite. The ferrule 46 is deformed and made to seal the joint with the source housing 44 using, for example, a compression nut 48 that is threadedly attached to the source housing 44. Other means of attaching the hollow needle electrode 14 may be used, as will be known to those of skill in the art in light of the present disclosure.

The hollow needle electrode 14 is electrically connected to a high voltage power source 50 through a current stabilization resistor that creates the electrical potential between the tip of the hollow needle electrode 14 and the skimmer plate 16 in close proximity to the aperture 18 of the skimmer plate 16 and prevents sporadic arcing. The high voltage power supply provides a direct current to the hollow needle electrode 14. The aperture 18 of the skimmer plate 16 will vary according to the amount of balance gas 22 flowing into the ion source 12, and the ability to remove the excess balance gas 22 from the first low pressure region 20. In one embodiment, the aperture 18 is about 100 microns.

An insulating cup 58 may be placed within the first low pressure region. The insulating cup 58 may be press fit to provide vacuum isolation for the aperture 18 of the skimmer plate 16 and the aperture 28 of the skimmer cone 30, while also providing a sufficient dielectric to provide electrical isolation of the apertures 28 from each other as well as from the source housing 44. The skimmer cone 30 is connected to a ring conductor that is electrically connected with a conducting epoxy. The skimmer cone 30 is electrically isolated from the source housing 44. The aperture 28 of the skimmer cone 30 must be aligned with the aperture 28 of the skimmer plate 16.

The balance gas 22 is fed into the hollow needle electrode 14 by connecting the outlet 54 of a gas chromatograph (not depicted) via a low dead volume miniature union 52. The gas chromatograph serves to replace the bulk gas from a contaminated sample with a carrier gas that is higher in ionization potential than the contaminants. The output from the gas chromatograph is the balance gas 22, which contains the resolved contaminants and the bulk gas in the chromatographic carrier gas.

In operation, a potential of several kilo volts is applied to the hollow needle electrode 14 creating a corona discharge between the tip of the hollow needle electrode 14 and the skimmer plate 16. The corona discharge ionizes the balance gas 22 flowing through the interior of the hollow needle electrode 14 as it exits the same. The balance gas 22 has a higher ionization potential than the contaminants within the balance gas 22. The ionized balance gas 22 undergoes charge exchange with the contaminants, generating contaminant ions that are extracted through the aperture 28 of the skimmer plate 16. Contaminant ions are extracted by both the potential difference between electrode plates and by the herding force created by the pressure difference between the first and second low pressure regions (20, 32).

Figure 3:
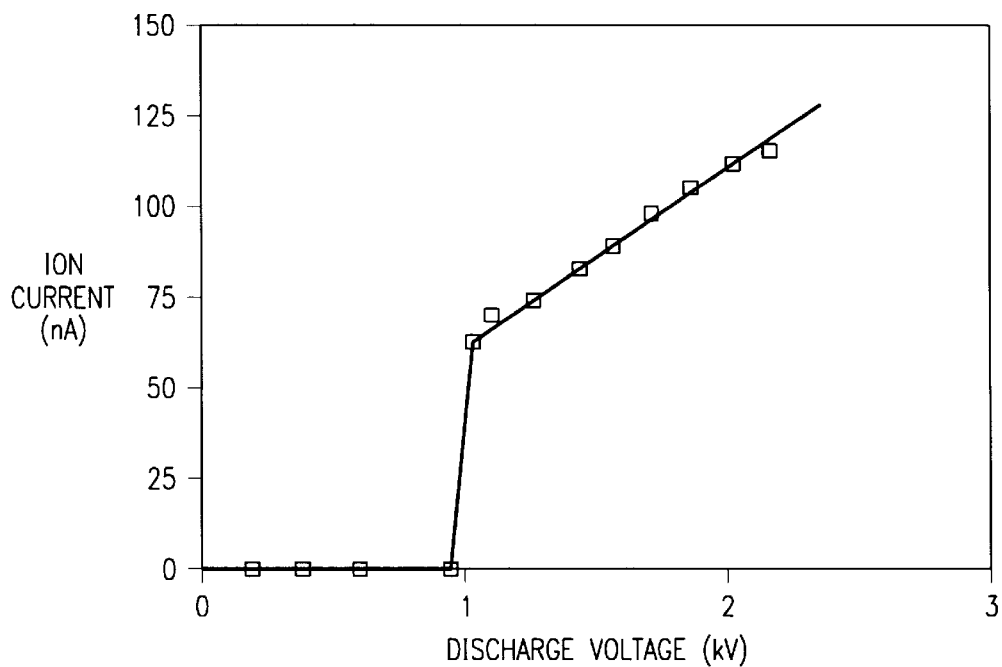
FIG. 3 is a graph showing the ionic current measured by the atmospheric pressure ionization source coupled to a mass spectrometer of the present invention.

FIG. 3 is a graph showing positive ion current reaching the skimmer cone 30 in the first low pressure region 20 prior to the mass filter 38 as a function of the potential of the hollow needle electrode 14. The Y-axis is the ion current in nano-amperes, and the X-axis is the discharge voltage in kilo volts. An ion current that is linear to the applied voltage following the initiation of the corona discharge is detected at the first ion focusing lens 34.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An trace analysis apparatus for measuring contaminants of interest in a bulk gas comprising:
   a gas chromatograph that replaces a bulk gas in a composition of bulk gas including contaminants in a bulk gas stream with a carrier gas having higher ionization potential than that of the contaminants of interest;
   a hollow electrode for initiating atmospheric-pressure ionization of substantially only said contaminants of interest by an electrical discharge connected to said gas chromatograph;
   a plate adjacent to and electrically isolated from said hollow electrode;
   a mass spectrometer connected to said hollow electrode; and
   a detector integrally connected to said mass spectrometer for measuring an ion current to detect the extent of contamination from said contaminants of interest.

2. The apparatus as recited in claim 1 wherein said hollow electrode is a low work function metal.

3. The apparatus as recited in claim 2 wherein said hollow electrode low work function metal is platinum.

4. The apparatus as recited in claim 2 wherein said hollow electrode low work function metal is stainless steel.

5. The apparatus as recited in claim 2 wherein said hollow electrode low work function metal is tungsten.

6. The apparatus as recited in claim 2 wherein said hollow electrode low work function metal is silver.

7. An trace analyzer apparatus for measuring contaminants of interest in a bulk gas comprising:
   a gas chromatograph that replaces a bulk gas in a composition of bulk gas including contaminants in a bulk gas stream with a carrier gas having higher ionization potential than that of the contaminants of interest;
   a low work function metal hollow electrode for initiating atmospheric-pressure ionization of substantially only said contaminants of interest by an electrical discharge connected to said gas chromatograph;
   a plate adjacent to and electrically isolated from said hollow electrode;
   a mass spectrometer connected to said hollow electrode; and
   a detector integrally connected to said spectrometer for measuring an ion current to detect the extent of contamination from said contaminants of interest.

8. The apparatus as recited in claim 7 wherein said hollow electrode low work function metal is platinum.

9. The apparatus as recited in claim 7 wherein said hollow electrode low work function metal is stainless steel.

10. The apparatus as recited in claim 7 wherein said hollow electrode low work function metal is tungsten.

11. The apparatus as recited in claim 7 wherein said hollow electrode low work function metal is silver.

12. An trace analyzer apparatus for measuring contaminants of interest in a bulk gas comprising:
    a gas chromatograph that replaces a bulk gas in a composition of bulk gas including contaminants in a bulk gas stream with a carrier gas having a higher ionization potential than that of the contaminants of interest;
    a low work function metal hollow needle electrode for initiating atmospheric-pressure ionization of substantially only said contaminants of interest by an electrical discharge;
    a source housing attached to said gas chromatograph;
    an insulator surrounding and sealing said hollow electrode into said source housing;
    a plate adjacent said hollow electrode, wherein a corona is formed between said hollow electrode and surrounding said insulator;
    a mass spectrometer connected to said hollow electrode; and
    a detector integrally connected to said mass spectrometer, wherein said detector measures the ion current of a gas that is input through said hollow needle electrode and detects the extent of contamination of said contaminants of interest with said gas flow.

13. The apparatus as recited in claim 12 wherein said hollow electrode low work function metal is platinum.

14. The apparatus as recited in claim 12 wherein said hollow electrode low work function metal is stainless steel.

15. The apparatus as recited in claim 12 wherein said hollow electrode low work function metal is tungsten.

16. The apparatus as recited in claim 12 wherein said hollow electrode low work function metal is silver.

17. The apparatus as recited in claim 12 wherein said insulator is a deformable ferrule.

18. A trace analysis method useful in semiconductor chemical processing for measuring contaminants of interest in a bulk gas comprising the steps of:
    replacing a bulk gas in a composition of bulk gas including contaminants in a bulk gas stream with a carrier gas having higher ionization potential than that of the contaminants of interest;
    initiating atmospheric-pressure ionization of said contaminants of interest by an electrical discharge that contains substantial components of electrical potential high as the ionization potential of said contaminants of interest but substantially none high as the ionization potential of said carrier gas;
    separating said ionized contaminants of interest from the remainder of said carrier gas; and
    measuring an ion current to detect the extent of contamination from said contaminants of interest.

19. The method of claim 18 further including the step of further separating predetermined ones of said ionized contaminants of interest from said ion current prior to detection of the extent of contamination.

20. The method of claim 18 wherein said step of replacing is provided by a gas chromatograph.

21. The method of claim 20 wherein said step of initiating ionization is provided by a hollow electrode.

22. The method of claim 19 wherein said step of replacing is provided by a gas chromatograph.

23. The method of claim 22 wherein said step of initiating ionization is provided by a hollow electrode.

* * * * *